United States Patent
Wham et al.

(10) Patent No.: US 10,653,471 B2
(45) Date of Patent: *May 19, 2020

(54) SYSTEMS AND METHODS FOR ARC DETECTION AND DRAG ADJUSTMENT

(71) Applicant: COVIDIEN LP, Mansfield, CO (US)

(72) Inventors: Robert H. Wham, Boulder, CO (US); James A. Gilbert, Boulder, CO (US); Craig A. Keller, Boulder, CO (US); Brian L. Roberts, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 822 days.

This patent is subject to a terminal disclaimer.

(21) Appl. No.: 15/354,322

(22) Filed: Nov. 17, 2016

(65) Prior Publication Data
US 2017/0065328 A1 Mar. 9, 2017

Related U.S. Application Data

(63) Continuation of application No. 14/182,797, filed on Feb. 18, 2014, now Pat. No. 9,498,275.
(Continued)

(51) Int. Cl.
*A61B 18/10* (2006.01)
*A61B 18/12* (2006.01)
(Continued)

(52) U.S. Cl.
CPC ...... *A61B 18/1206* (2013.01); *A61B 18/1402* (2013.01); *A61B 2018/00702* (2013.01);
(Continued)

(58) Field of Classification Search
CPC ........ A61B 18/1206; A61B 2018/1213; A61B 2018/00696; A61B 2018/00702;
(Continued)

(56) References Cited

U.S. PATENT DOCUMENTS

| | | | |
|---|---|---|---|
| 4,114,623 | A | 9/1978 | Meinke et al. |
| 4,818,954 | A | 4/1989 | Flachenecker et al. |

(Continued)

FOREIGN PATENT DOCUMENTS

| | | |
|---|---|---|
| CN | 204092172 U | 1/2015 |
| CN | 204971565 U | 1/2016 |

(Continued)

OTHER PUBLICATIONS

European Search Report, Application No. EP 14 15 9837 dated May 28, 2014.

(Continued)

*Primary Examiner* — Jaymi E Della

(57) ABSTRACT

Controlling a level of electrosurgical energy provided to tissue based on detected arcing patterns or impedance changes. The drag force imposed on an electrode or blade of an electrosurgical instrument may be controlled by adjusting the level of electrosurgical energy based on the arcing patterns or impedance changes. The arcing patterns or impedance changes may be detected by sensing and analyzing voltage and/or current waveforms of the electrosurgical energy. The current and/or voltage waveform analysis may involve calculating impedance based on the voltage and current waveforms and calculating changes in impedance over time. The waveform analysis may involve detecting harmonic distortion using FFTs, DFTs, Goertzel filters, polyphase demodulation techniques, and/or bandpass filters. The waveform analysis may involve determining a normalized difference or the average phase difference between the voltage and current waveforms.

16 Claims, 13 Drawing Sheets

Related U.S. Application Data

(60) Provisional application No. 61/784,141, filed on Mar. 14, 2013.

(51) Int. Cl.
*A61B 18/14* (2006.01)
*A61B 18/00* (2006.01)

(52) U.S. Cl.
CPC ............ *A61B 2018/00755* (2013.01); *A61B 2018/00779* (2013.01); *A61B 2018/00827* (2013.01); *A61B 2018/00869* (2013.01); *A61B 2018/00892* (2013.01); *A61B 2018/1213* (2013.01)

(58) Field of Classification Search
CPC ........... A61B 2018/00708; A61B 2018/00827; A61B 2018/00892; A61B 2018/00875
See application file for complete search history.

(56) References Cited

U.S. PATENT DOCUMENTS

| | | | |
|---|---|---|---|
| 5,886,890 A | 3/1999 | Ishida et al. | |
| 6,740,079 B1 | 5/2004 | Eggers et al. | |
| 7,393,354 B2 | 7/2008 | Buchman, II et al. | |
| 7,621,909 B2 | 11/2009 | Buchman, II et al. | |
| 7,651,492 B2 | 1/2010 | Wham | |
| 8,016,824 B2 | 9/2011 | Buchman, II et al. | |
| 9,498,275 B2 | 11/2016 | Wham et al. | |
| 2004/0092927 A1 | 5/2004 | Podhajsky et al. | |
| 2005/0119646 A1 | 6/2005 | Scholl et al. | |
| 2006/0058783 A1* | 3/2006 | Buchman, III | A61B 18/1402 606/42 |
| 2007/0129716 A1* | 6/2007 | Daw | A61B 18/1206 606/34 |
| 2009/0254077 A1 | 10/2009 | Craig | |
| 2009/0275938 A1 | 11/2009 | Roggan et al. | |
| 2012/0083779 A1 | 4/2012 | Hosier | |

FOREIGN PATENT DOCUMENTS

| | | |
|---|---|---|
| GB | 2486343 A | 6/2012 |
| WO | 07/067522 A2 | 6/2007 |

OTHER PUBLICATIONS

Chinese Office Action and English language translation in Appl. No. CN 201410095367.6 dated Mar. 20, 2017.

* cited by examiner

SYSTEMS AND METHODS FOR ARC DETECTION AND DRAG ADJUSTMENT

CROSS REFERENCE TO RELATED APPLICATION

The present application is a continuation application of U.S. patent application Ser. No. 14/182,797, filed on Feb. 18, 2014, now U.S. Pat. No. 9,498,275 which claims the benefit of and priority to U.S. Provisional Patent Application No. 61/784,141, filed on Mar. 14, 2013, the entire contents of which are incorporated herein by reference.

BACKGROUND

1. Technical Field

The present invention relates generally to electrosurgical systems and methods and, more particularly, to systems and methods for arc detection and drag adjustment.

2. Background of Related Art

Electrosurgical instruments have become widely used by surgeons in recent years. Accordingly, a need has developed for equipment that is easy to handle and operate, reliable, and safe. Most electrosurgical instruments typically include a hand-held instrument that applies radio-frequency (RF) alternating current to the target tissue. The alternating current is returned to the electrosurgical source via a return electrode pad positioned under a patient (i.e., a monopolar system configuration) or a return electrode positionable in bodily contact with or immediately adjacent to the surgical site (i.e., a bipolar system configuration). One very common waveform produced by the RF source yields a predetermined electrosurgical effect that results in the cutting of tissue or the stopping or reducing of bleeding.

In particular, electrosurgical fulguration comprises the application of an electric spark to biological tissue, for example, human flesh or the tissue of internal organs, with minimal cutting. Generally, fulguration is used to dehydrate, shrink, necrose, or char the tissue. As a result, this technique is primarily used to stop bleeding and oozing. These operations are generically embraced by the term "Coagulation." Meanwhile, electrosurgical cutting includes the use of the applied electric spark to cut tissue. Electrosurgical sealing includes utilizing both pressure and electrosurgically generated heat to melt the tissue collagen into a fused mass that prevents bleeding from the fused tissue.

As used herein the term "electrosurgical pencil" is intended to include monopolar electrosurgical instruments which have a handpiece which is attached to an active electrode and are used to coagulate, cut, and/or seal tissue. The electrosurgical pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed, or slanted distal end. Typically, electrodes of this sort are known in the art as "blade," "loop" or "snare," or "needle" or "ball" electrodes.

The handpiece of the electrosurgical instrument is connected to a suitable electrosurgical source, such as an electrosurgical generator, which produces radio-frequency alternating current necessary for the operation of the electrosurgical instrument. In general, when an operation is performed on a patient with an electrosurgical instrument, alternating current from the electrosurgical generator is conducted through the active electrode to the tissue at the site of the operation (the target tissue) and then through the patient to a return electrode. The return electrode is typically placed at a convenient place on the patient's body and is attached to the generator by a conductive material.

During a surgical procedure, an operator moves the electrode or blade of the electrosurgical instrument through the tissue at a desired speed depending on, among other things, the skill of the operator and the type of tissue that is being treated. Oftentimes, however, the speed at which the operator can move the electrode of the electrosurgical instrument through the tissue is limited by a force that opposes the movement of the electrosurgical instrument through the tissue. This force is referred to as drag. The drag not only limits the operator's ability to more quickly and efficiently complete a surgical procedure, but also limits the operator's ability to easily adapt during the surgical procedure to different tissue types and characteristics, which may present different drag profiles.

SUMMARY

The present disclosure relates to electrosurgical systems and methods that provide an operator with the ability to set the drag or drag profile exhibited by the cutting tip of an electrosurgical instrument, as the cutting tip is advanced through tissue.

In aspects, the present disclosure features a method of controlling electrosurgical energy provided by an electrode of an electrosurgical instrument to tissue. The method includes delivering electrosurgical energy to the electrode of the electrosurgical instrument, sensing arcing patterns between the electrode and tissue, and controlling the level of electrosurgical energy delivered to the electrode based on the sensed arcing patterns.

The method of controlling electrosurgical energy may include determining drag based on the sensed arcing patterns, and controlling the level of electrosurgical energy delivered to the electrode based on the determined drag and a predetermined drag value. Controlling the level of energy delivered to the electrode may include increasing the power of the electrosurgical energy delivered to the electrode if the determined drag is greater than the predetermined drag value and decreasing the power of the electrosurgical energy delivered to the electrode if the determined drag is less than the predetermined drag value. Controlling the level of energy delivered to the electrode may include adjusting the duty cycle of the RF waveform to change the drag. The method of controlling electrosurgical energy may include receiving the predetermined drag value from a user interface, or reading the predetermined drag value from a bar code, an RFID tag, or a memory associated with the electrosurgical instrument.

The arcing patterns may be sensed by sensing at least one of the voltage and current waveforms of the electrosurgical energy delivered to the electrode, and detecting harmonic distortion of the at least one of the voltage and current waveforms. The harmonic distortion may be detected by filtering with respect to frequency at least one of the voltage and current waveforms. For example, the harmonic distortion may be detected by applying a Fast Fourier Transform (FFT), a Discrete Fourier Transform (DFT), a Goertzel filter, or a narrow-band filter to at least one of the voltage and current waveforms. Detecting harmonic distortion may involve detecting at least one of the second, third, and fifth harmonics of at least one of the voltage and current waveforms.

The arcing patterns may be sensed by sensing the voltage and current waveforms of the electrosurgical energy delivered to the electrode, and calculating the normalized difference between the voltage and current waveforms.

The arcing patterns may be sensed by sensing the voltage and current of the electrosurgical energy, calculating the phase difference between the voltage and current of the electrosurgical energy, calculating the average phase difference over a predetermined time interval, and sensing the arcing patterns based on the average phase difference.

The arcing patterns may be sensed by sensing the voltage and current of the electrosurgical energy, calculating impedance based on the sensed voltage and current, and detecting the arcing patterns based on the change in calculated impedance over time. For example, sensing arcs starting and stopping over time scales of 1 ms may indicate rapid changes in impedance.

The arcing patterns may be sensed by sensing impedance between the electrode and tissue, detecting arcing if a low inductive impedance is sensed, detecting a loss of arcing if a high capacitive impedance is sensed, and detecting contact with tissue if a resistive impedance is sensed.

The method of controlling electrosurgical energy provided by an electrode of an electrosurgical instrument to tissue may include determining drag based on the sensed impedance, and controlling the level of electrosurgical energy delivered to the electrode based on the determined drag and a predetermined drag value. Determining drag may include determining a low level of drag if a high capacitive impedance is sensed, and determining a high level of drag if a primarily resistive impedance is sensed.

Controlling the level of energy delivered to the electrode may include increasing the power of the electrosurgical energy delivered to the electrode if the determined drag force is greater than the predetermined drag force setting and decreasing the power of the electrosurgical energy delivered to the electrode if the determined drag force is less than the predetermined drag force setting.

In further aspects, the present disclosure features an electrosurgical generator for providing electrosurgical energy to an electrode of an electrosurgical instrument. The electrosurgical generator includes an output stage that provides electrosurgical energy to the electrode of the electrosurgical instrument, a sensor that senses arcing patterns of the electrosurgical energy provided to the tissue by the electrode, and a controller coupled to the output stage and the sensor. The controller controls the level of electrosurgical energy delivered to the electrode based on the sensed arcing patterns.

The controller may determine a drag force on the electrode of the electrosurgical instrument based on the sensed arcing patterns and control the level of electrosurgical energy delivered to the electrode based on the determined drag force and a drag force setting. The electrosurgical generator may include a user interface that provides the drag force setting to the controller in response to a user selection.

The sensor may include at least one of a voltage sensor and a current sensor, and the controller may detect harmonic distortion of at least one of the voltage and current waveforms output from at least one of the voltage and current sensors, respectively. The controller detects harmonic distortion of at least one of the voltage and current waveforms by filtering with respect to the frequency of at least one of the voltage and current waveforms. For example, the controller may detect harmonic distortion of at least one of the voltage and current waveforms by applying a Goertzel filter, a narrow-band filter, or a Fast Fourier Transform (FFT) to at least one of the voltage and current waveforms. The controller may detect arcing patterns by sensing at least one of the second, third, and fifth harmonics of at least one of the voltage and current waveforms.

The sensor may include a voltage sensor and a current sensor that sense the voltage and current waveforms of the electrosurgical energy, and the controller may calculate a normalized difference between the voltage and current waveforms to sense arcing patterns.

The sensor may include a voltage sensor and a current sensor that sense the voltage and current waveforms of the electrosurgical energy, and the controller may calculate impedance based on the sensed voltage and current waveforms, and determine arcing patterns based on the change in calculated impedance over time.

The sensor may sense impedance between the electrode and tissue, and the controller may detect arcing if a low inductive impedance is sensed, detect a loss of arcing when a high capacitive impedance is sensed, and detect contact with tissue if a resistive impedance is sensed.

The sensor may include a voltage sensor that senses a voltage waveform of the electrosurgical energy and a current sensor that senses a current waveform of the electrosurgical energy, and the controller may calculate a phase difference between the voltage and current waveforms, calculate an average phase difference between the voltage and current waveforms over a predetermined time interval, and determine arcing patterns based on the average phase difference.

The controller may determine drag based on a sensed arcing pattern or the sensed impedance, and control the level of electrosurgical energy delivered to the electrode based on the determined drag and a predetermined drag value. The controller may calculate a phase difference between the voltage and current waveforms, calculate an average phase difference between the voltage and current waveforms over a predetermined time interval, and determine arcing patterns based on the average phase difference.

The controller may control the level of electrosurgical energy delivered to the electrode by increasing the power delivered to the electrode if the determined drag is greater than the predetermined drag value and by decreasing the power of the electrosurgical energy delivered to the electrode if the determined drag is less than the predetermined drag value.

In still further aspects, the present disclosure features an electrosurgical system including an electrosurgical instrument that delivers electrosurgical energy to tissue and an electrosurgical generator coupled to the electrosurgical instrument. The electrosurgical generator includes an output stage that generates the electrosurgical energy, a sensor that senses arcing patterns of the electrosurgical energy provided to the tissue by the electrode of the electrosurgical instrument, and a controller coupled to the output stage and the sensor. The controller controls the level of electrosurgical energy delivered to the electrode based on the sensed arcing patterns.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Figure 1:
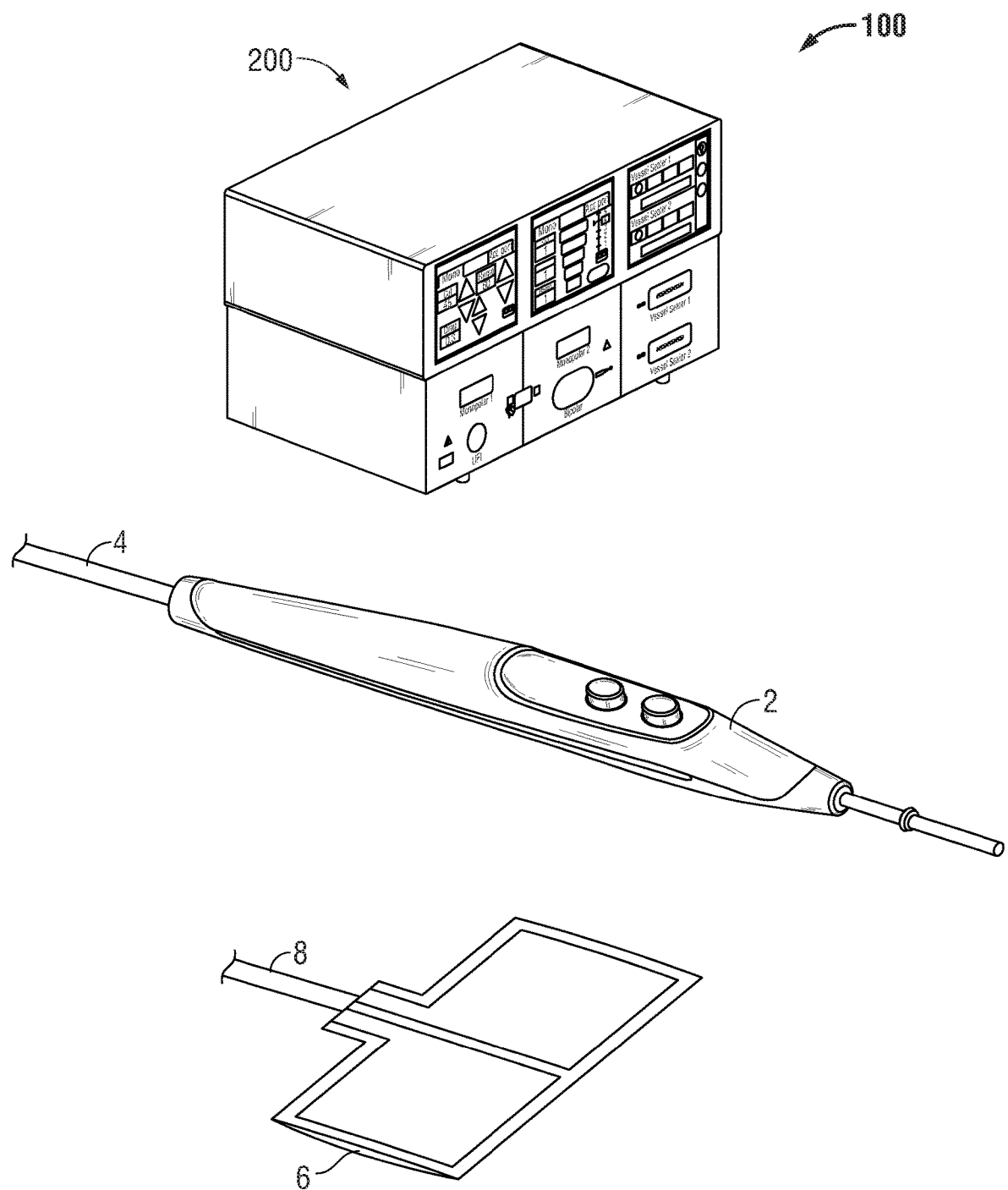
FIG. 1 is a perspective view of an electrosurgical system including an electrosurgical generator, an electrosurgical instrument, and a return pad, according to embodiments of the present disclosure.

Embodiments of the present disclosure are described in detail with reference to the drawing figures wherein like reference numerals identify similar or identical elements. As used herein, the term "distal" refers to the portion that is being described which is farther from a user, while the term "proximal" refers to the portion that is being described which is closer to a user.

The systems and methods of the present disclosure allow an operator to control the drag force imposed on a monopolar electrosurgical instrument depending on, among other things, the skill of the operator and the different types and characteristics of tissue that are encountered by the operator during a surgical procedure. The present disclosure is directed to systems and methods for detecting arcing patterns or impedance changes and adjusting the power of the electrosurgical generator so that the drag force imposed on the blade of an electrosurgical instrument can be controlled to a user-selected drag force level based on the detected arcing patterns or impedance changes. The arcing or impedance patterns may be detected by sensing voltage and/or current waveforms used to cut tissue and analyzing the sensed voltage and/or current waveforms. The current and/or voltage waveform analysis may involve calculating impedance or complex impedance and determining patterns in the calculated impedance.

Alternatively, the waveform analysis may involve detecting harmonic distortion using FFTs, DFTs, Goertzel filters, polyphase demodulation techniques, and/or narrow-band filters. The harmonic distortion may be detected by monitoring one or more frequency components of the voltage and current waveforms, such as the second, third, and/or fifth harmonics of the voltage and current waveforms. The frequency components may also include side bands associated with the harmonics of the fundamental RF frequency.

Time domain techniques may also be employed to detect arcing patterns. In some embodiments, the difference between the voltage and current waveforms, e.g., the normalized difference between the voltage and current waveforms, may be calculated to detect arcing patterns. In other embodiments, arcing patterns may be detected by sensing complex impedance patterns. A low inductive impedance may indicate arcing, a high capacitive impedance may indicate that there is no arcing, and a resistive tissue impedance may indicate direct contact with tissue.

A generator according to the present disclosure can perform monopolar and/or bipolar electrosurgical procedures, including vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cutting, blending, division, etc.) and procedures (e.g., monopolar, bipolar, vessel sealing). In embodiments, the generator may be embedded, integrated, or otherwise coupled to the electrosurgical instruments providing for an all-in-one electrosurgical apparatus.

FIG. 1 is a schematic illustration of an electro surgical system 100 according to the present disclosure. The system 100 may include one or more monopolar electrosurgical instruments 2 having one or more electrodes (e.g., electrosurgical cutting probe, ablation electrodes, etc.) for treating tissue of a patient. Electrosurgical alternating current is supplied to the instrument 2 by a generator 200 via a supply line 4 that is connected to an active terminal 330 (FIG. 3) of the generator 200, allowing the instrument 2 to coagulate, ablate, cut, and/or otherwise treat tissue. The alternating current is returned to the generator 200 through a return electrode 6 via a return line 8 at a return terminal 332 (FIG. 3) of the generator 200. The system 100 may include a plurality of return electrodes 6 that are disposed on a patient to minimize the chances of tissue damage by maximizing the overall contact area with the patient. In addition, the generator 200 and the return electrode 6 may be configured to monitor contact between the return electrodes 6 and tissue to ensure that sufficient contact exists between them to further minimize chances of unintended tissue damage.

Figure 2:
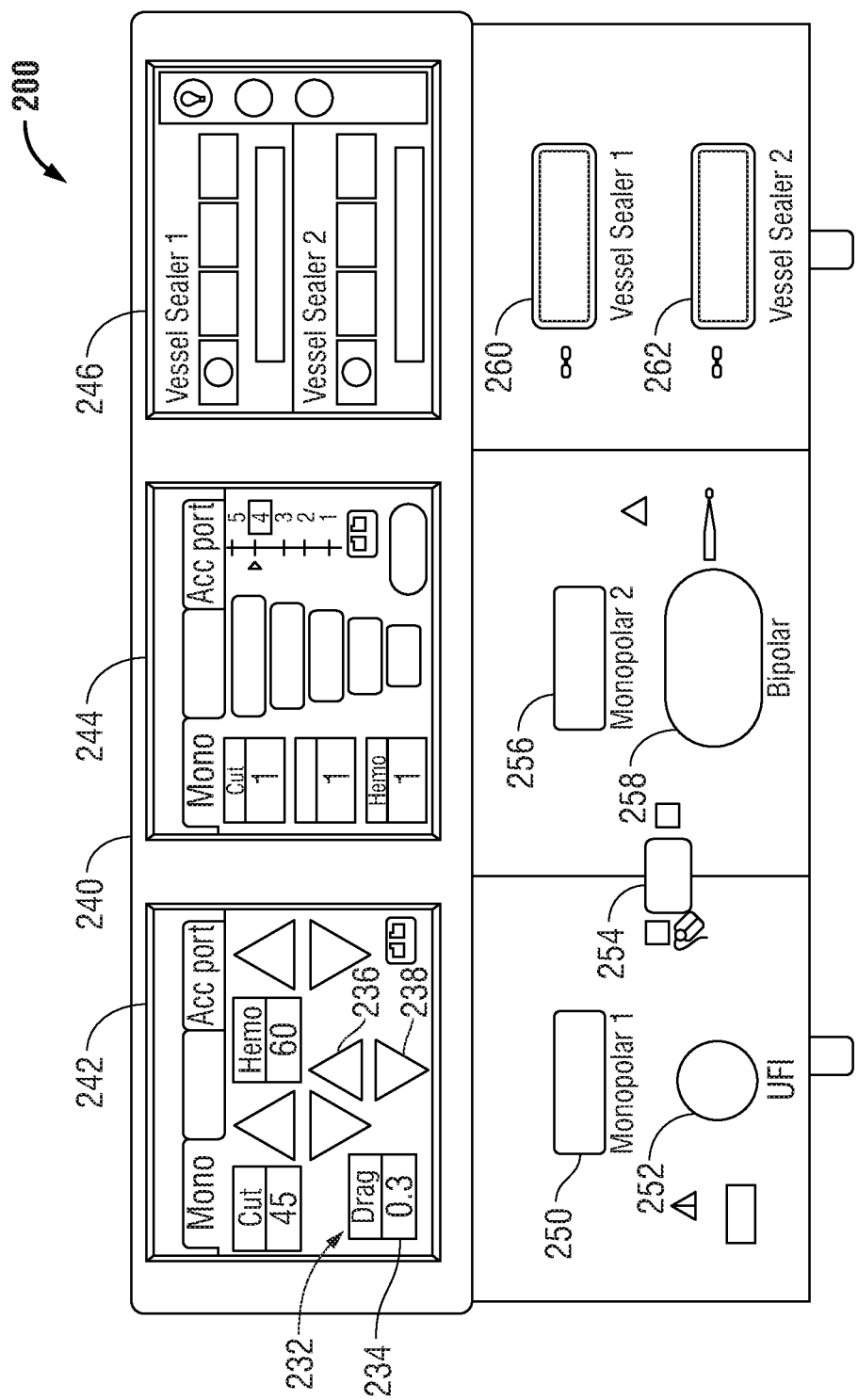
FIG. 2 is a front view of the electrosurgical generator of FIG. 1.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 10). The connectors 250-262 may include various detection devices that can read (e.g., scan, decode, etc.) identifying information encoded or otherwise recorded on or within the plugs or cables of the instruments. The connectors 250-262 are configured to decode the information encoded on the plugs corresponding to the operating parameters of particular instruments allowing the generator 200 to preset energy delivery settings or drag settings based on the connected instrument. In embodiments, data may be encoded in bar codes, electrical components (e.g., resistors, capacitors, etc.), RFID chips, magnets, non-transitory storage (e.g., non-volatile memory, EEPROM, etc.), which may then be coupled to or integrated into the plug. Corresponding detection devices may include, but are not limited to, bar code readers, electrical sensors, RFID readers, Hall Effect sensors, memory readers, etc., and any other suitable decoders configured to decode data.

The generator 200 includes one or more display screens 242, 244, 246 for providing the user with a variety of output information (e.g., intensity settings, treatment complete indicators, etc.). Each of the screens 242, 244, 246 is associated with corresponding connectors 250-262. The generator 200 includes suitable input controls (e.g., buttons, activators, switches, touch screen, etc.) for controlling the generator 200. The display screens 242, 244, 246 may be configured as touch screens that display a corresponding menu for the electrosurgical instruments (e.g., electrosurgical forceps, etc.). The user can then makes inputs by simply touching corresponding menu options.

Screen 242 controls monopolar output and the devices connected to the connectors 250 and 252. The screen 242 includes a portion 232 that allows an operator to set a desired drag force for the monopolar device connected to connector 250. Specifically, the screen 242 includes buttons 236 and 238, which allow an operator to increase or decrease the drag force setting. The screen 242 also displays the current drag force setting 234, which, as shown in FIG. 2, is 0.3. The connector 250 is configured to couple to a monopolar electrosurgical instrument (e.g., an electrosurgical pencil) and connector 252 is configured to couple to a foot switch (not shown). The foot switch provides for additional inputs, which may replicate inputs of the generator 200. Screen 244 controls monopolar and bipolar output and the devices connected to connectors 256 and 258. Connector 256 is configured to couple to other monopolar instruments. Connector 258 is configured to couple to a bipolar instrument (not shown). Screen 246 controls vessel sealers connected to connectors 260 and 262.

Figure 3:
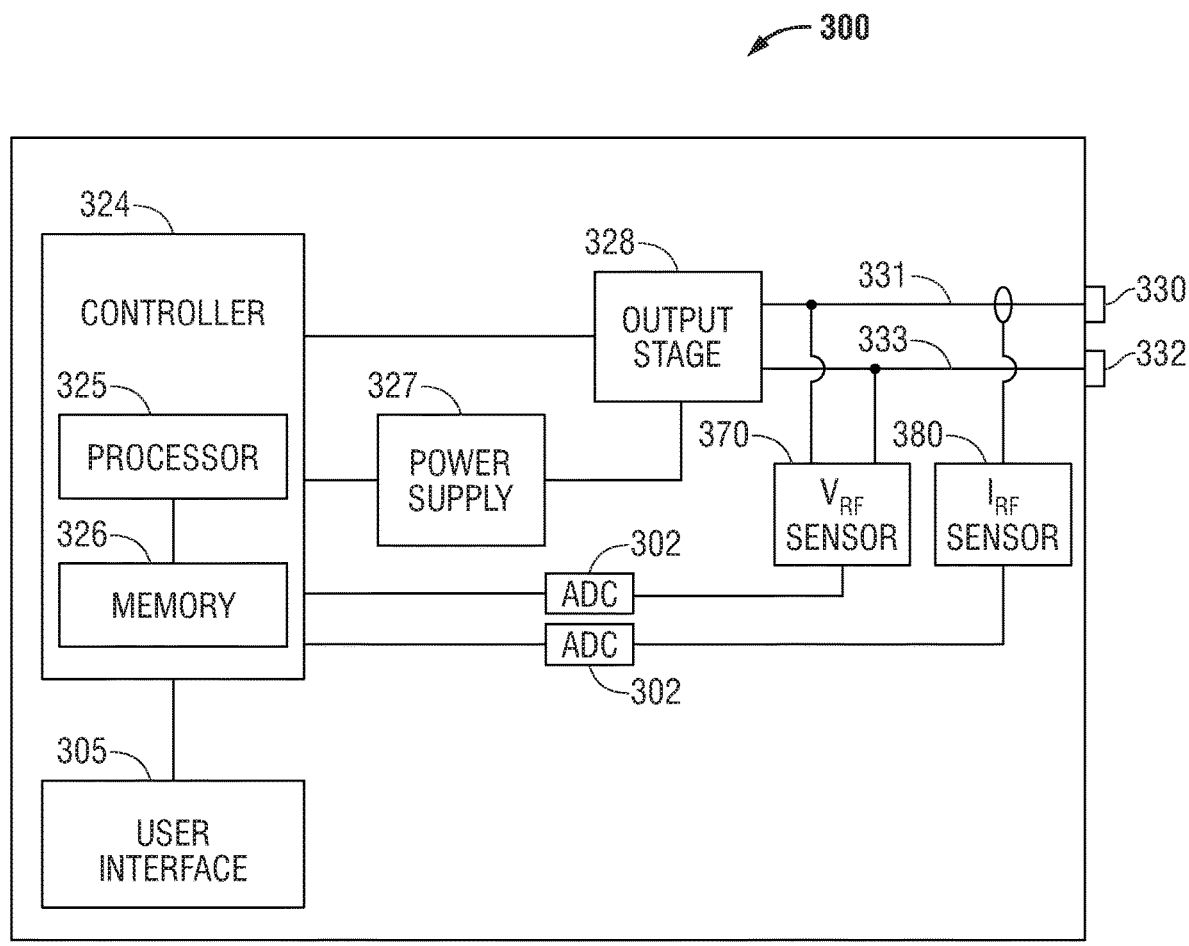
FIG. 3 is a schematic block diagram of the electrosurgical generator of FIG. 1.

FIG. 3 shows a schematic block diagram of the generator circuitry 300 of the generator 200 of FIGS. 1 and 2, which is configured to output electrosurgical energy. The generator circuitry 300 includes a user interface 305, a controller 324, a power supply 327, and an output stage 328. The power supply 327 may be a direct current high voltage power supply and may be connected to an AC source (e.g., line voltage). The power supply 327 provides high voltage DC power to an output stage 328, which then converts high voltage DC power into electrosurgical alternating current and provides the electrosurgical energy to the active terminal 330. The alternating current is returned to the output stage 328 via the return terminal 332. The output stage 328 is configured to operate in a plurality of modes, during which the generator circuitry 300 outputs corresponding waveforms having specific duty cycles, peak voltages, crest factors, etc. In other embodiments, the generator circuitry 300 may be based on other types of suitable power supply topologies.

The controller 324 includes a processor 325 (e.g., a microprocessor) operably connected to a memory 326, which may include transitory type memory (e.g., RAM) and/or non-transitory type memory (e.g., flash media and disk media). In embodiments, the controller 324 may further include a field-programmable gate array (FPGA) for performing real-time analysis of the delivered current and/or voltage waveforms, as described below. The processor 325 includes an output port that is operably connected to the power supply 327 and/or output stage 328 allowing the processor 325 to control the output of the generator circuitry 300 according to either open- and/or closed-loop control schemes. Those skilled in the art will appreciate that the processor 325 may be substituted by any logic processor (e.g., control circuit) adapted to perform the calculations and/or set of instructions discussed herein.

The generator circuitry 300 implements a closed-loop feedback control system, in which a plurality of sensors measure a variety of tissue and generator output properties (e.g., tissue impedance, tissue temperature, output power, current and/or voltage, etc.), and provide feedback to the controller 324. The controller 324 then signals the power supply 327 and/or output stage 328, which then adjusts the DC power supply and/or output stage, respectively. The controller 324 also receives input signals from the user interface 305 of the generator circuitry 300. The controller 324 utilizes input signals received through the user interface 305 to adjust power outputted by the generator circuitry 300 and/or performs other control functions thereon. According to the present disclosure, an operator may input a desired drag setting via the user interface 305. For example, some surgeons prefer high drag to reduce the probably of accidentally cutting into undesired areas. Thus, these surgeons may input a desired drag setting via the user interface 305 that provides a high drag level. In general, this would slow the rate of cutting.

In embodiments, the desired drag setting or a default drag setting may be programmed into memory disposed within the instrument 2 or stored in a bar code or radio-frequency identification (RFID) tag disposed on the instrument 2. The desired drag setting may also be deduced from the surgeon's rate of cutting. For example, the controller 324 may determine the average drag experienced by the surgeon based on arc patterns, set the desired drag setting to the average drag, and adjust the output power or voltage to achieve the desired drag setting. The controller 324 may perform these functions during an auto-drag mode, which may be set by the surgeon.

The controller 324 retrieves and uses the desired drag setting to adjust the power of the electrosurgical output from the output stage 328 based on sensed arcing patterns and/or the impedance patterns between the electrosurgical instrument 2 and the tissue.

The generator circuitry 300 according to the present disclosure includes an RF current sensor 380 and an RF voltage sensor 370. The RF current sensor 380 is coupled to the active terminal 330 and provides measurements of the RF current supplied by the output stage 328. The RF voltage sensor 370 is coupled to the active and return terminals 330 and 332, and provides measurements of the RF voltage supplied by the output stage 328. In embodiments, the RF voltage and current sensors 370 and 380 may be coupled to active lead 331 and return lead 333, which interconnect the active and return terminals 330 and 332 to the output stage 328, respectively.

The RF voltage and current sensors 370 and 380 provide the sensed RF voltage and current signals, respectively, to analog-to-digital converters (ADCs) 302. The ADCs 302 sample the sensed RF voltage and current signals and provide digital samples of the sensed RF voltage and current signals to the controller 324, which then may adjust the output of the power supply 327 and/or the output stage 328 in response to the digital samples of the sensed RF voltage and current signals. Various components of the generator circuitry 300, namely, the output stage 328 and the RF voltage and current sensors 370 and 380, may be disposed on a printed circuit board (PCB).

Figure 4:
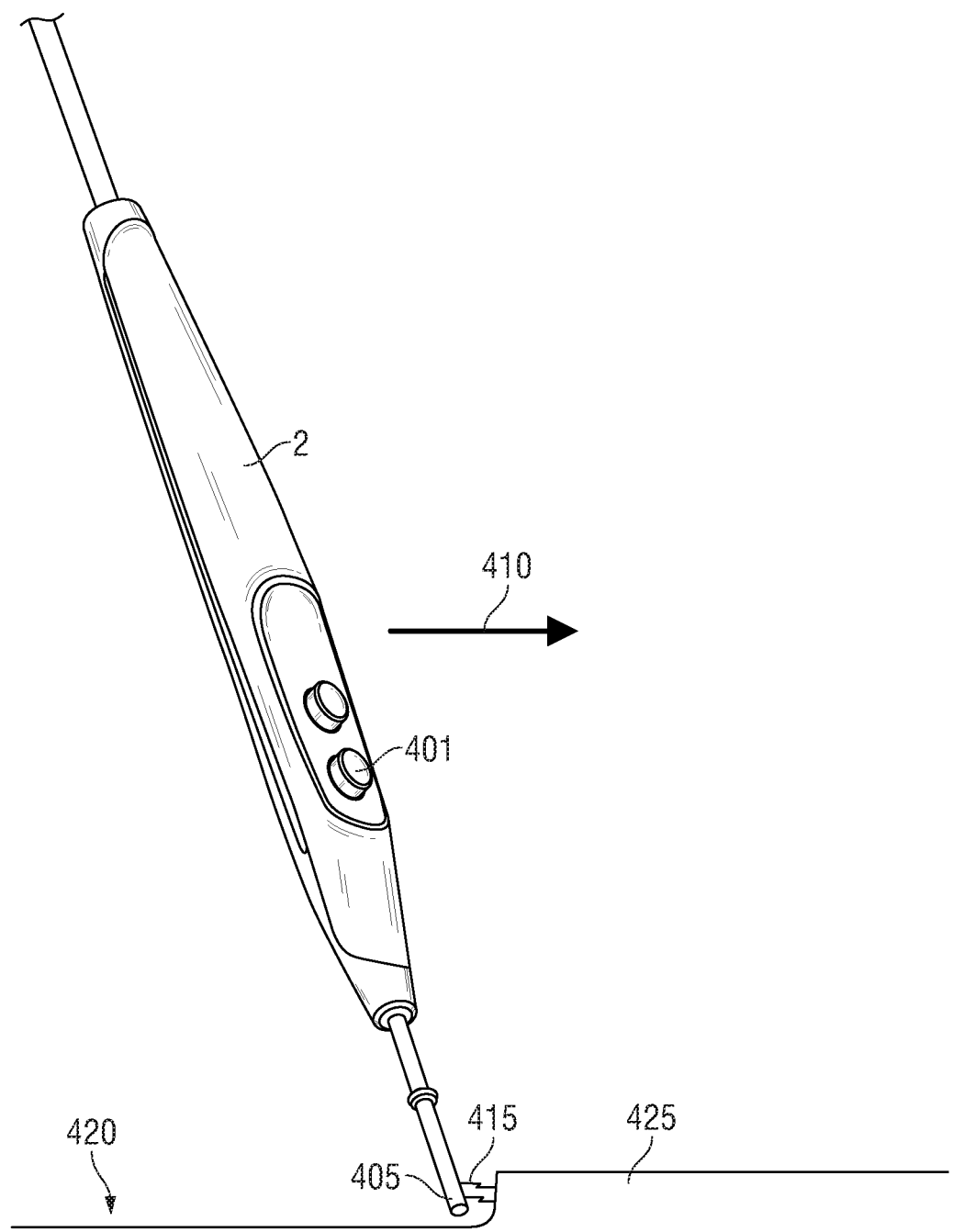
FIG. 4 is a diagram illustrating arcing during an electrosurgical procedure using the electrosurgical instrument of FIG. 1.

FIG. 4 is a diagram illustrating arcing during a monopolar cutting procedure performed by the electrosurgical instrument 2. A surgeon sets the electrosurgical instrument 2 to a desired drag value via the user interface 305 of the generator circuitry 300 and activates the electrosurgical instrument 2 by depressing the activation switch 401, thus permitting alternating current to be transmitted to the cutting tip or blade 405. The surgeon then commences the electrosurgical procedure by touching the cutting tip or blade 405 to the target tissue 420.

There is evidence that the process of monopolar cutting precedes the blade 405 of the instrument 2 by arcing 415 to the fresh tissue 425 ahead of the blade 405, thus vaporizing the fresh tissue 425 before the blade 405 makes contact with other fresh tissue 425. In other words, arcs 415 form as the blade gets close to the boundary edge of the tissue 425 and extinguish once the tissue 425 is vaporized and the boundary edge moves farther from the blade so that the arcs 415 are extinguished. If the blade is moving slower than the maximum rate of tissue removal, this results in a pattern of arcing, followed by a capacitive state (an "open circuit") as the arcing extinguishes when all tissue within range has been removed. If the blade is moving faster than the maximum rate of tissue removal, a resistive state is achieved as the blade 405 comes into contact with fresh tissue 425.

If the movement rate of the blade 405 in the direction 410 is slow compared to the power or voltage setting of the generator 200, then the arc 415 vaporizes the tissue 420 and extinguishes before the blade 405 moves close enough to the fresh tissue 425 to reestablish an arc 415. The repeated process of moving the blade 405, creating an arc 415, and extinguishing the arc 415 creates a detectable arc pulse pattern. This repeated process may be detected as a change from an arc 415 to a capacitive impedance.

If, on the other hand, the movement rate of the blade 405 is fast compared to the power or voltage setting of the generator 200, then arcing may be reduced because of the constant contact between the blade 405 and the tissue 425 or arcing may be at a constant level. Contact between the blade 405 and the tissue 425 increases the drag of the tissue on the blade 405. According to embodiments of the present disclosure, these arcing patterns are detected and used to determine the drag of the tissue on the blade 405. The power level of the alternating current applied to the tissue is then adjusted to achieve a desired drag value.

It is contemplated that electrosurgical instrument 2 may be provided with an audible or visible (i.e., light) feedback system (not shown) which would signal to the operator when the drag acting on the cutting tip or blade 405 is near, is equal to, or has surpassed a predetermined drag level. For example, generator 200 and/or the electrosurgical instrument 2 may include a buzzer and/or light which are set to be activated when the sensed drag reaches a certain predetermined drag value or falls within a range of drag values. In this manner, the operator can focus on the target tissue site and be alerted, for example, by the sound of a buzzer, by the flashing of a light, or by both, when the resistance acting against the advancement of the cutting tip 405 has become greater than the predetermined drag value.

Figure 5A:
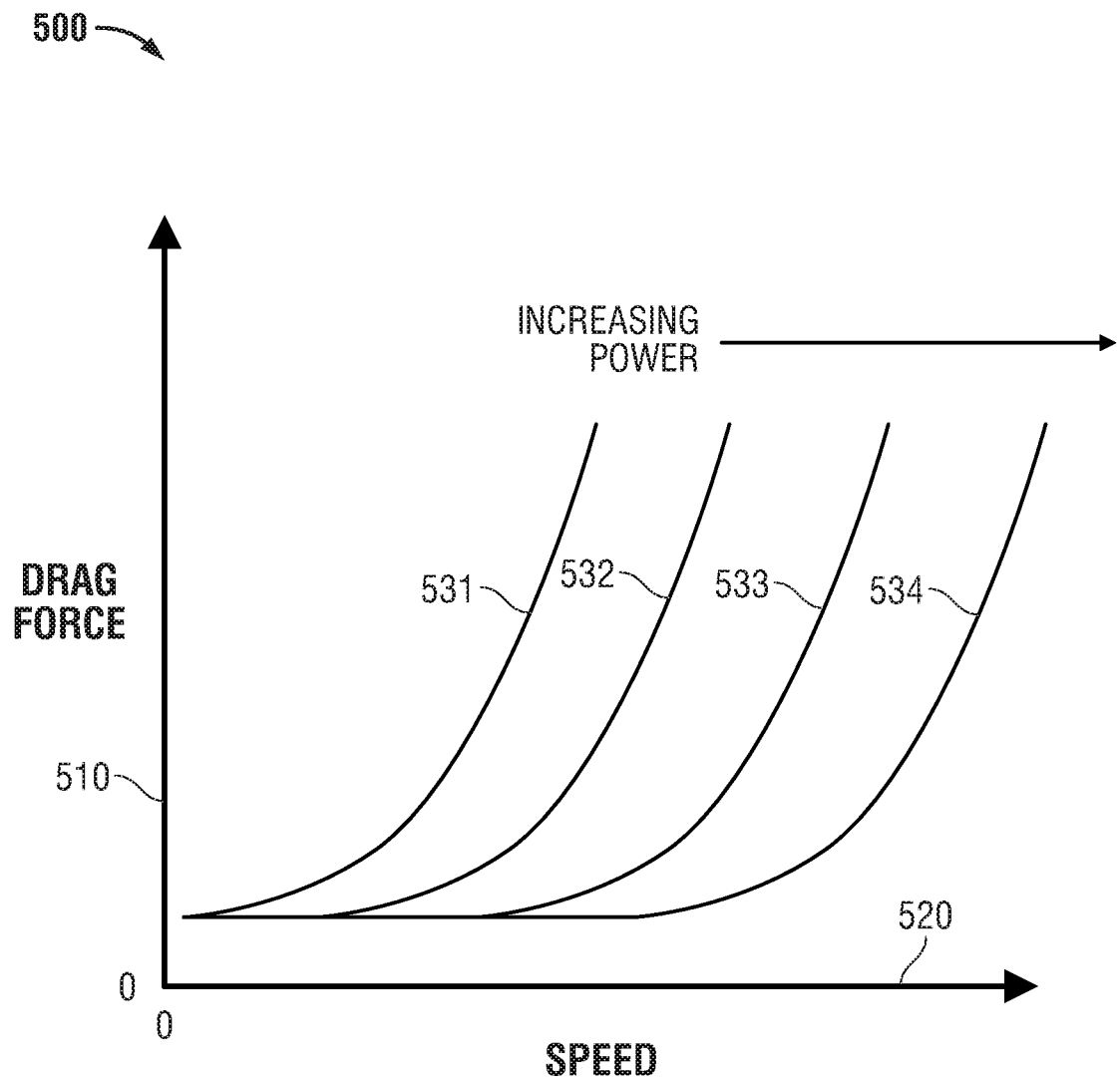
FIG. 5A is a graphical diagram illustrating the relationships among drag force, speed, and electrosurgical power for the electrosurgical procedure illustrated in FIG. 4.

FIG. 5A is a graphical diagram 500 illustrating the relationship among drag force, speed, and electrosurgical power for the electrosurgical instrument 2 during a cutting procedure. The graphical diagram 500 includes a first axis 510 indicating the drag force of the tissue on the blade 405 and a second axis 520 indicating the speed or movement rate of the blade 405 as it cuts tissue. The graphical diagram 500 shows drag profile curves 531-534, each of which represents the relationship between drag force and speed at a constant power level, arranged in order of increasing power levels.

Each of the drag profile curves 531-534 show that the drag force increases significantly as the speed of the electrosurgical instrument 2 is increased for a given constant power level. In other words, when the surgeon cuts tissue with the electrosurgical pencil at low and moderate speeds, there is little resistance to the movement of the electrosurgical pencil through the tissue. As the speed of cutting increases, the resistance remains relatively low until a point at which the drag force increases sharply as shown by the drag profile curves 531-534.

The drag force increases sharply at the end of the drag profile curves because the arc front does not fully vaporize the tissue 425 before the blade 405 moves into contact with the tissue 425. As shown in FIG. 5A, increasing the power allows for a higher speed with minimal drag because increasing the power increases the tissue vaporization ahead of the blade. For example, if the surgeon makes a shallow cut, then a small amount of power is needed to vaporize the small amount of tissue, thus reducing drag for a given power level. If the surgeon increases the depth of the cut, then more power is needed to vaporize the larger amount of tissue to maintain the same drag level.

According to the present disclosure, the drag or the cutting speed of the electrosurgical instrument is controlled based on the arcing patterns or characteristics of the arcs formed between the electrode or cutting tip of the electrosurgical instrument and the tissue and/or based on the impedance sensed between the electrode and tissue. The arcing pattern may be a pulse pattern of arcing and loss of arcing. The loss of arcing may occur when there is an "open circuit" or a relatively high capacitive impedance between the cutting tip of the electrosurgical instrument 2 and tissue 425 (e.g., when the blade is moved relatively slowly) or when there is a resistive impedance between the cutting tip of electrosurgical instrument 2 and tissue when the electrosurgical instrument is moved rapidly and comes into contact with tissue.

Thus, the high capacitive impedance between the blade 405 and the tissue 425 indicates low drag because the cutting tip of the electrosurgical instrument 2 is too far from the tissue to create an arc and the power of the electrosurgical energy is at a high level. A resistive impedance between the blade 405 and the tissue 425 indicates high drag because the cutting tip of the electrosurgical instrument 2 is in contact with the tissue 425 and the power of the electrosurgical energy is at a low level.

In some embodiments, the arcing patterns may include three states or modes: (1) loss of arcing to tissue, (2) arcing to tissue, and (3) contact with tissue. In other embodiments, the arcing patterns include the shape or other characteristic of the voltage and/or current waveform of the electrosurgical energy delivered to the tissue. For example, the shape or other characteristic of the harmonic distortion during arcing may be useful to predict when the cutting tip may come in contact with tissue. The arcing patterns may be macro arcing patterns in the RF waveform at the 100 μs to 1 ms scale and/or micro arcing pattern in the RF waveform at the 2 to 10 μs scale.

A variety of techniques may be employed to detect the arcing patterns. When an arc forms between the electrode of the electrosurgical instrument and tissue, the voltage and/or current waveforms of the electrosurgical energy that flows to the tissue may change considerably. The techniques for detecting arcing patterns involve detecting these changes in the voltage and/or current waveforms.

Figure 5B:
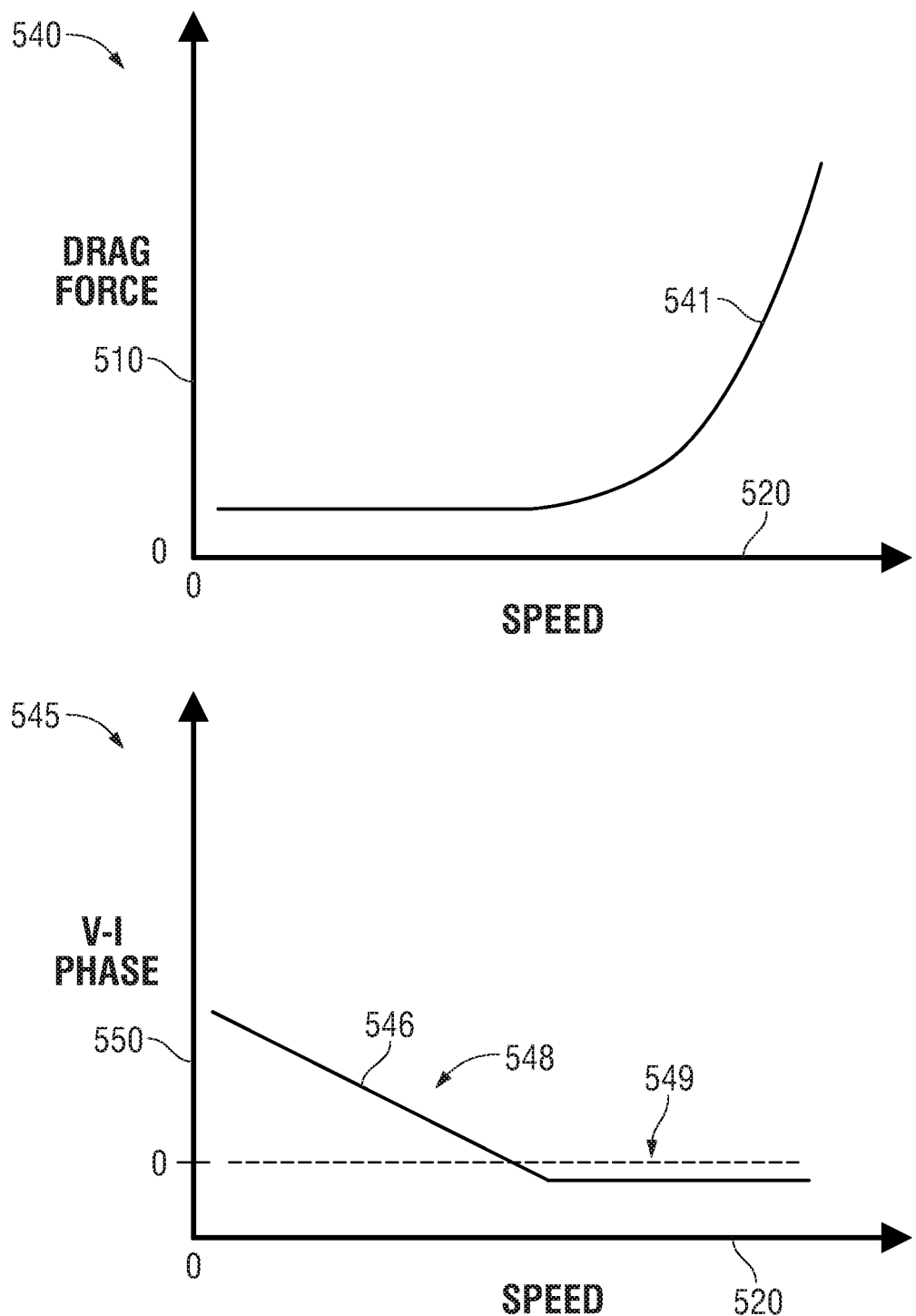
FIG. 5B shows graphical diagrams illustrating the relationships among speed, drag force, and phase between the voltage and current of the electrosurgical energy delivered to the tissue for the surgical procedure illustrated in FIG. 4.

FIG. 5B shows graphical diagrams 540 and 545 illustrating the relationships among speed, drag force, and the phase between the voltage and current of the electrosurgical energy delivered to tissue for the surgical procedure illustrated in FIG. 4. Similar to FIG. 5A, graphical diagram 540 shows the drag force as a function of a velocity ramp (i.e., constant acceleration) when constant electrosurgical power is applied to tissue having constant thickness. As shown, when the speed reaches a particular value, the drag force 541 increases sharply. Graphical diagram 545 shows the phase difference between the voltage and current of the electrosurgical power (i.e., axis 550) applied to the tissue as a function of speed (i.e., axis 520) under the same conditions described above with respect to graphical diagram 540. As shown, the phase difference 546 decreases linearly (i.e., the ramp 548) and then becomes constant 549 at about the same speed at which the drag force 541 begins to increase.

The ramp 548 in the phase difference 546 may be caused by the transition from not cutting to cutting at a maximum speed. Thus, the electrosurgical power may be controlled by monitoring the phase difference between the voltage and current of the electrosurgical power and adjusting the output electrosurgical power to maintain a desired phase difference and thus a desired cutting effect. In some embodiments, if a desired cutting effect occurs at higher speed versus power ratios, the electrosurgical power may be modulated or pulsed to lower the speed versus power ratio for a sufficient amount of time to determine the phase difference and thus the location on the graphical diagram 545. This information may then be used to maintain a particular cutting effect by adjusting the output electrosurgical power.

Figure 6:
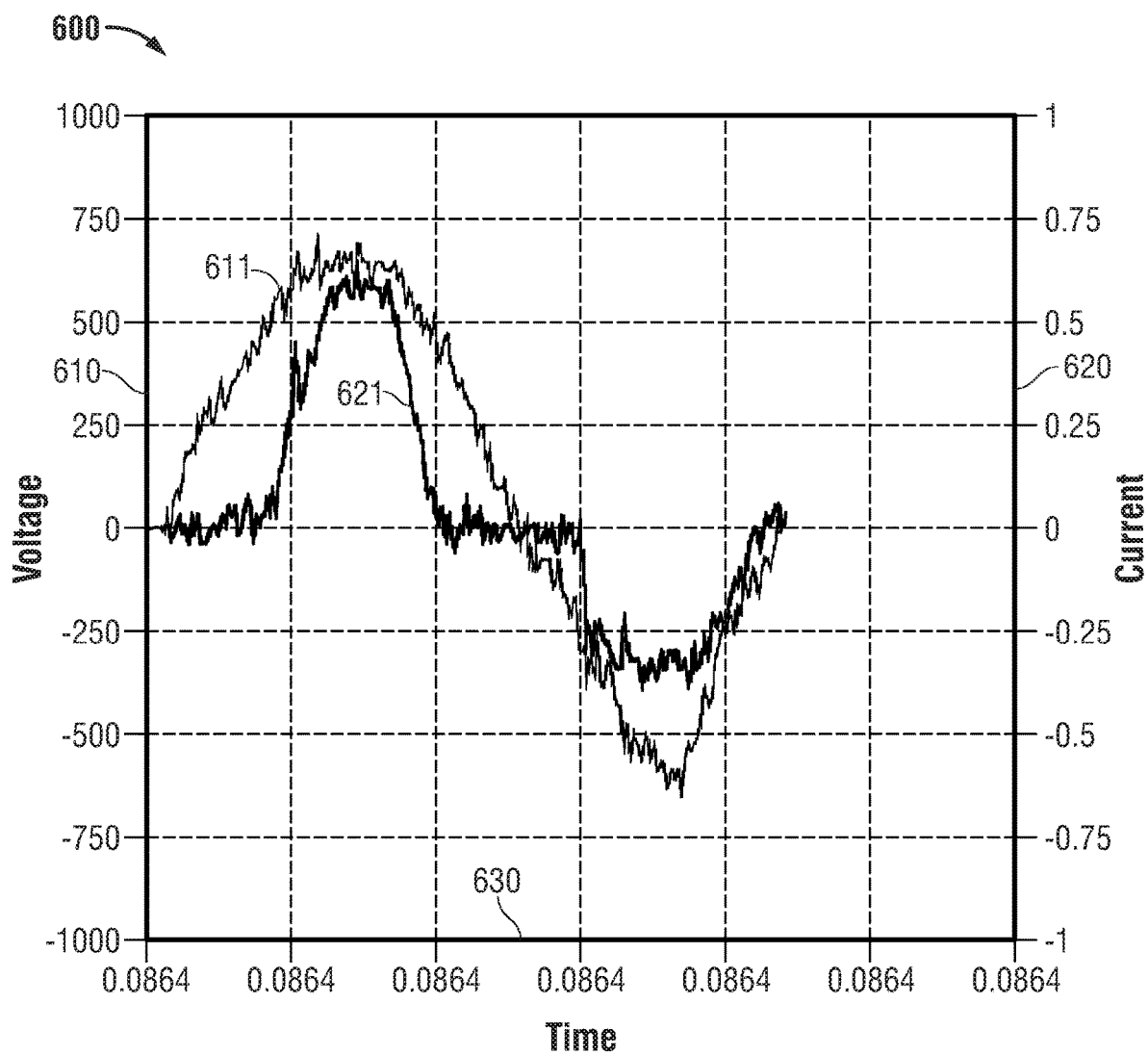
FIG. 6 is a graphical diagram of the voltage and current of an arcing pattern during an electrosurgical cutting procedure.

FIG. 6 is a graphical diagram 600 illustrating one technique for detecting arcing patterns between the electrosurgical instrument 2 and tissue during a surgical procedure. The graphical diagram 600 includes a first axis 610 indicating the voltage of the electrosurgical energy as measured by the voltage sensor 370 of FIG. 3, a second axis 620 indicating the current as measured by the current sensor 380 of FIG. 3, and a third axis 630 indicating the time. The voltage waveform 611 and the current waveform 621 were measured by the voltage sensor 370 and the current sensor 380, respectively, during arcing. The arcing is shown by the difference between the voltage waveform 611 and the current waveform 621. The shape of the current waveform 621 shows the current flow during the arc and, when the voltage waveform 611 drops, the arc is extinguished, and then re-established. The current waveform 621 shows distinct harmonic distortion while the voltage waveform 611 shows little distortion.

Thus, the controller 324 may be configured to detect arcing when the controller 324 detects harmonic distortion or a particular shape or other characteristic of the harmonic distortion in the current waveform 621. Alternatively, the controller 324 may be configured to detect arcing when the controller 324 detects harmonic distortion or a particular shape or other characteristic of the harmonic distortion in the voltage waveform 611. The amount of harmonic distortion in the voltage and current waveforms depends on the Thevenin output impedance compared to the load resistance of the arc events. If the output impedance were small compared to the load, then the voltage would be relatively harmonic free, while the current would be distorted. If, on the other hand, the output impedance were large compared to the load impedance, then the current would be relatively harmonic free, while the voltage would be distorted (e.g., the voltage would droop as the current rises).

The harmonic distortion of the voltage and current waveforms may be detected using FFT or DFT frequency decomposition techniques (e.g., using multiple single frequency DFT algorithms), Goertzel filters, or one or more bandpass filters, demodulation filters, which may be implemented in the controller 324. For example, the one or more single frequency DFT algorithms or the one or more narrowband bandpass filters may be configured for one or more harmonic frequencies that are associated with particular arcing patterns or characteristics, which indicate the level of drag of the tissue on the blade 405. These filters may monitor the second, third, and/or fifth harmonics of the voltage and current waveforms of the electrosurgical energy. In some embodiments, particular harmonics may be detected using polyphase demodulation techniques, which use a type of decimating digital filter. A polyphase demodulation technique could be used to create series bandpass filters. According to the polyphase demodulation technique, the frequency or frequencies of interest are demodulated to baseband (DC frequency) and the amplitude is sensed at the frequency or frequencies of interest.

Time domain techniques may be used to detect arcing patterns. For example, the controller 324 may determine the normalized difference between the voltage and current waveforms of the electrosurgical energy. If the normalized difference exceeds a predetermined value, then arcing is detected. Otherwise, arcing is not detected. In embodiments, the controller 324 may incorporate an FPGA that performs real-time analysis of the voltage and current waveforms to enable real-time control of the power and/or waveform of the electrosurgical energy delivered to the tissue.

The arcing patterns may be detected based on the impedance calculated from the voltage sensed by the voltage sensor 370 and the current sensed by the current sensor 380. The arcing or impedance pattern would include a low impedance during an arc and a high impedance when the arc extinguishes.

The arcing patterns described above may be detected based on impedance calculated using sensed voltage and current waveforms and the phase shift between them. The impedance would include a low inductive impedance during arcing, a high capacitive impedance when not arcing, and a primarily resistive impedance during contact with tissue.

The arcing patterns described above may be detected based on measurement of the time-averaged phase shift between the voltage and current waveforms at the electrode. The average phase shift increases monotonically from a small value when the electrode is in resistive contact with the tissue, to progressively higher values as arcing occurs for a larger fraction of the measured time, to even higher values as steady arcing is gradually replaced with the capacitive coupling as the electrode-tissue separation or gap becomes large enough to extinguish the arcing.

In yet other embodiments, the arcing pattern described above may be detected by analyzing the phase characteristics of the voltage and current waveforms. For example, changes in phase between the voltage and current waveforms may indicate transitions between states of the arcing pattern. When voltage is applied to the electrode of the electrosurgical instrument and there is no arcing between the electrode and tissue, the voltage and current waveforms are substantially out of phase because the electrode and tissue appear like a capacitor. When an arc forms between the electrode and tissue, and when the electrode is passing at a very slow speed through the tissue, the average phase between the voltage and current waveforms continues to appear capacitive. As the speed of the electrode through the tissue increases, with the supplied power held constant, the average phase between the voltage and current waveforms decreases in an approximately linear relationship to the speed.

When the electrode speed exceeds the maximum cutting rate at the supplied power, the electrode remains in contact with the tissue and the phase difference between the voltage and current waveforms is approximately zero corresponding to a purely resistive circuit. Even if the contact between the electrode and the tissue is purely resistive, the measured phase will often include an inductive component due to the wires leading to the electrode and from the patient. This can lead to the measured phase between the voltage and current waveforms passing through zero and becoming somewhat negative.

The changes in phase between the voltage and current may be detected by the controller 324 using some of the techniques described above. For example, the controller 324 may include a zero-crossing detector in which the time between zero crossings of the current waveform is subtracted from the time of the zero crossing of the voltage waveform to obtain a time delay. Then, the time delay is converted to a phase shift based on the RF frequency. The phase shift between the voltage and current waveforms may also be detected by using a FFT, DFT, or Goertzel, by detecting the phase of each waveform at the specified frequency and then subtracting the voltage phase result from the current phase result. The phase may also be determined by feeding the sensed voltage and current waveforms to appropriate logic gates (e.g., AND gates), correlating the output from the logic gates, and averaging the correlated output from the logic gates. These computations may be performed in an FPGA of the controller 324.

In some embodiments, the controller 324 may maintain a given power setting and change the peak voltage or crest factor of the electrosurgical energy to achieve a desired drag force. In other embodiments, when the generated electrosurgical energy has a continuous waveform (e.g., in the cut mode), the RMS voltage may be adjusted to achieve a desired drag force. In yet other embodiments, the controller 324 may control the shape of the waveform of the electrosurgical energy generated by the output stage 328 based on the detected arcing or impedance patterns to achieve a desired drag force.

The controller 324 may control the drag force or cutting speed by controlling the output stage 328 to generate waveform shapes or other characteristics of the electrosurgical energy to achieve a desired drag force or cutting speed. For example, if the surgeon sets a maximum cutting speed (or sets a minimum drag force) having minimal coagulation, the controller 324 may generate cutting waveforms having a 100% duty cycle. If the surgeon decreases the cutting speed (or increases the drag force), then the controller 324 may generate a cutting waveform having a duty cycle less than 100% (e.g., 50% for blend mode, 25% for V-mode, which modulates the voltage of the coagulation waveform, and 4.7% for fulguration mode). The cutting waveform having a duty cycle less than 100% increases the crest factor, which provides more coagulation, but less cutting ability. The lower duty cycle modes also increase the peak voltage for the same power. Both the power and duty cycle may be adjusted together to keep the peak voltage consistent while reducing the cutting ability. If the peak voltage was not kept constant, then the arc distance would increase as the duty cycle was reduced. The controller 324 may initiate a cutting waveform having high power or a 100% duty cycle when tissue contact is sensed (i.e., resistive impedance is sensed), and then switch to a lower power or a duty cycle less than 100% to increase drag after the initial cut is started.

Figure 7:
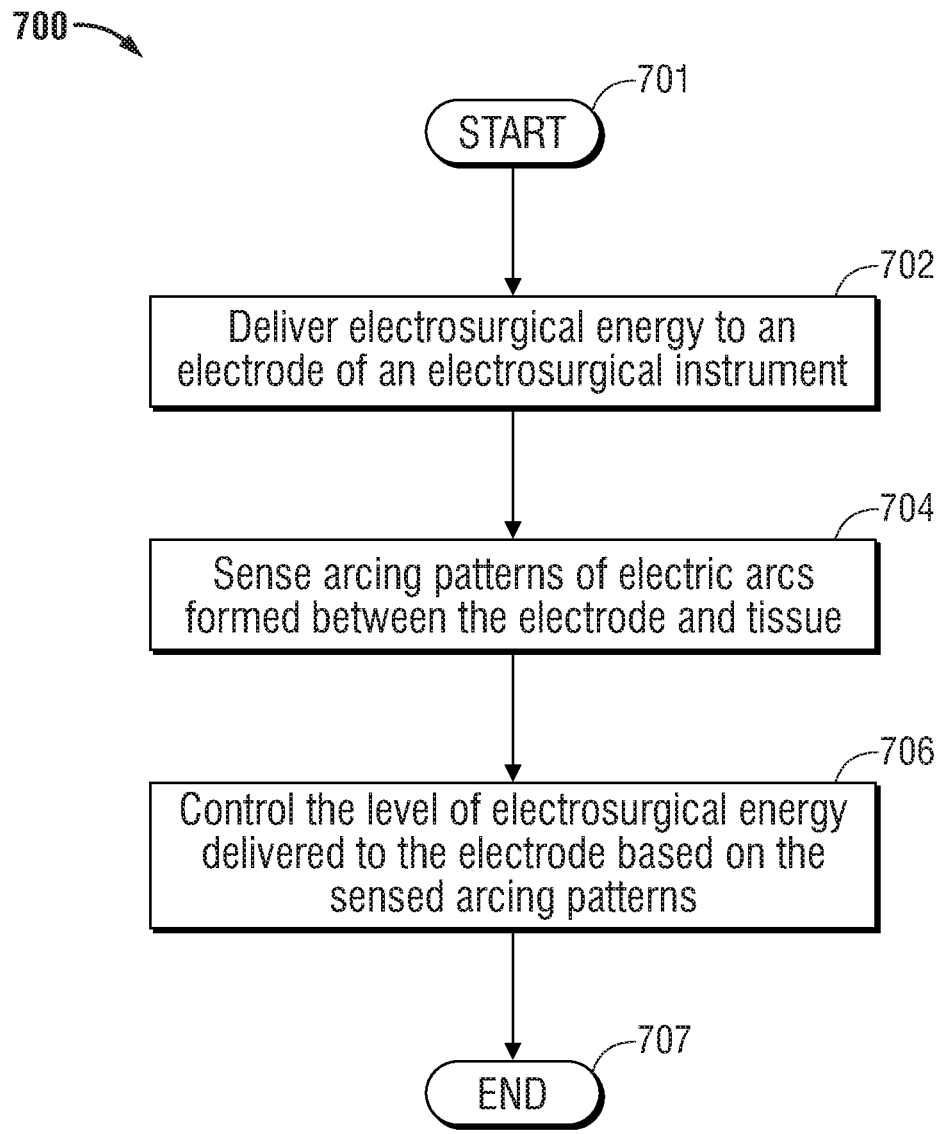
FIG. 7 is a flow diagram of a method of controlling electrosurgical energy delivered to an electrode of an electrosurgical instrument based on sensed arcing patterns according to embodiments of the present disclosure.

FIG. 7 is a flow diagram of a method 700 of controlling electrosurgical energy delivered to the electrode of an electrosurgical instrument based on sensed arcing patterns in accordance with embodiments of the present disclosure. After starting in step 701, electrosurgical energy is delivered to the electrode of the electrosurgical instrument in step 702. In step 704, arcing patterns of electric arcs formed between the electrode and tissue are sensed. As described above, a arcing patterns may be sensed in a variety of ways. In step 706, the level of electrosurgical energy delivered to the electrode is controlled based on the sensed arcing patterns. Then, in step 707, the method ends.

Figure 8:
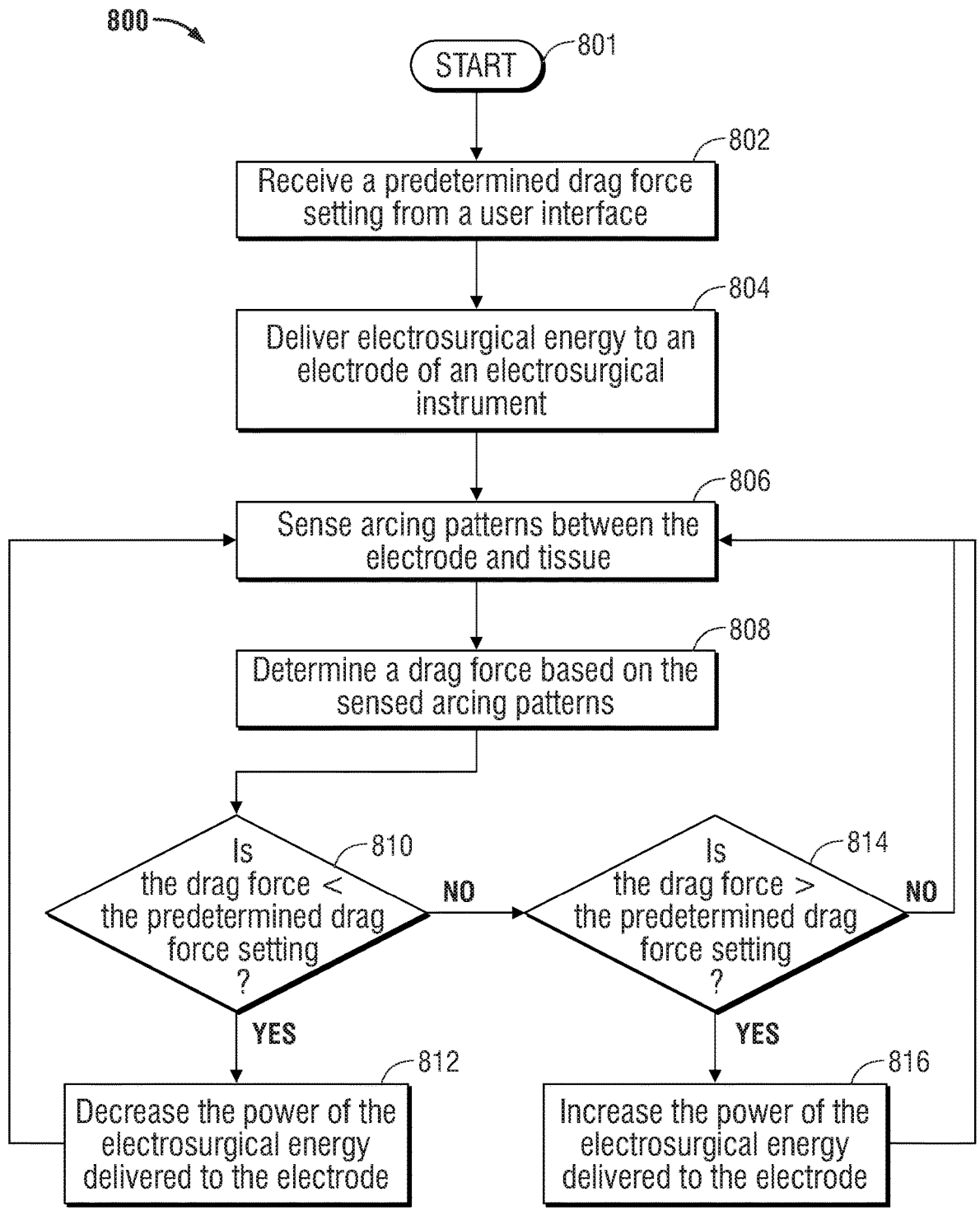
FIG. 8 is a flow diagram of a method of controlling electrosurgical energy to achieve a user-selected drag force based on sensed arcing patterns according to embodiments of the present disclosure.

FIG. 8 is a flow diagram of a method 800 of controlling electrosurgical energy to achieve a user-selected predetermined drag force based on sensed arcing patterns in accordance with embodiments of the present disclosure. After starting in step 801, a predetermined drag force setting is received from a user interface in step 802. In step 804, electrosurgical energy is delivered to an electrode of an electrosurgical instrument. In step 806, arcing patterns between the electrode and tissue are sensed. In step 808, a drag force is determined based on the sensed arcing patterns.

Next, in step 810, it is determined whether the determined drag force is less than the predetermined drag force setting. If so, the power of the electrosurgical energy delivered to the electrode is decreased or, alternatively, the duty cycle of the output RF waveform is decreased in step 812 and the method 800 returns to step 806. If it is determined that the determined drag force is not less than the predetermined drag force setting, it is determined whether the drag force is greater than the predetermined drag force setting, in step 814. If it is determined that drag force is greater than the predetermined drag force setting, then the power of the electrosurgical energy delivered to the electrode is increased or, alternatively, the duty cycle of the output RF waveform is increased in step 816 and the method 800 returns to step 806. If it is not determined that drag force is greater than the predetermined drag force setting, then the method 800 returns to step 806 to continue sensing arcing patterns between the electrode and tissue.

Figure 9:
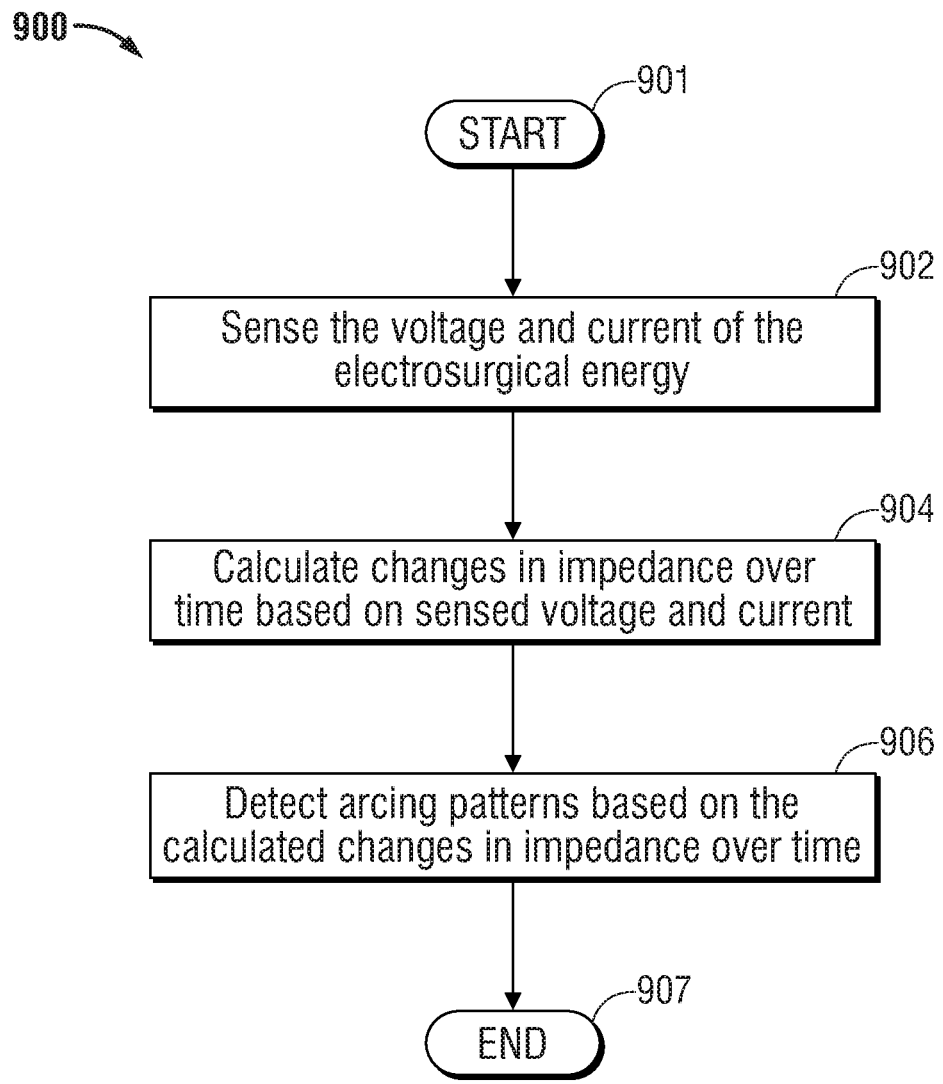
FIG. 9 is a flow diagram of a method of detecting arcing patterns based on impedance according to embodiments of the present disclosure.

FIG. 9 is a flow diagram of a method 900 of detecting arcing patterns based on impedance according to embodiments of the present disclosure. After starting in step 901, the voltage and current of the electrosurgical energy is sensed 902, e.g., by the voltage and current sensors 370, 380 of FIG. 3. In step 904, changes in impedance over time is calculated, e.g., by the controller 324, based on the sensed voltage and current. Then, before ending at step 907, arcing patterns are detected in step 906, e.g., by the controller 324, based on the calculated changes in impedance over time.

Figure 10:
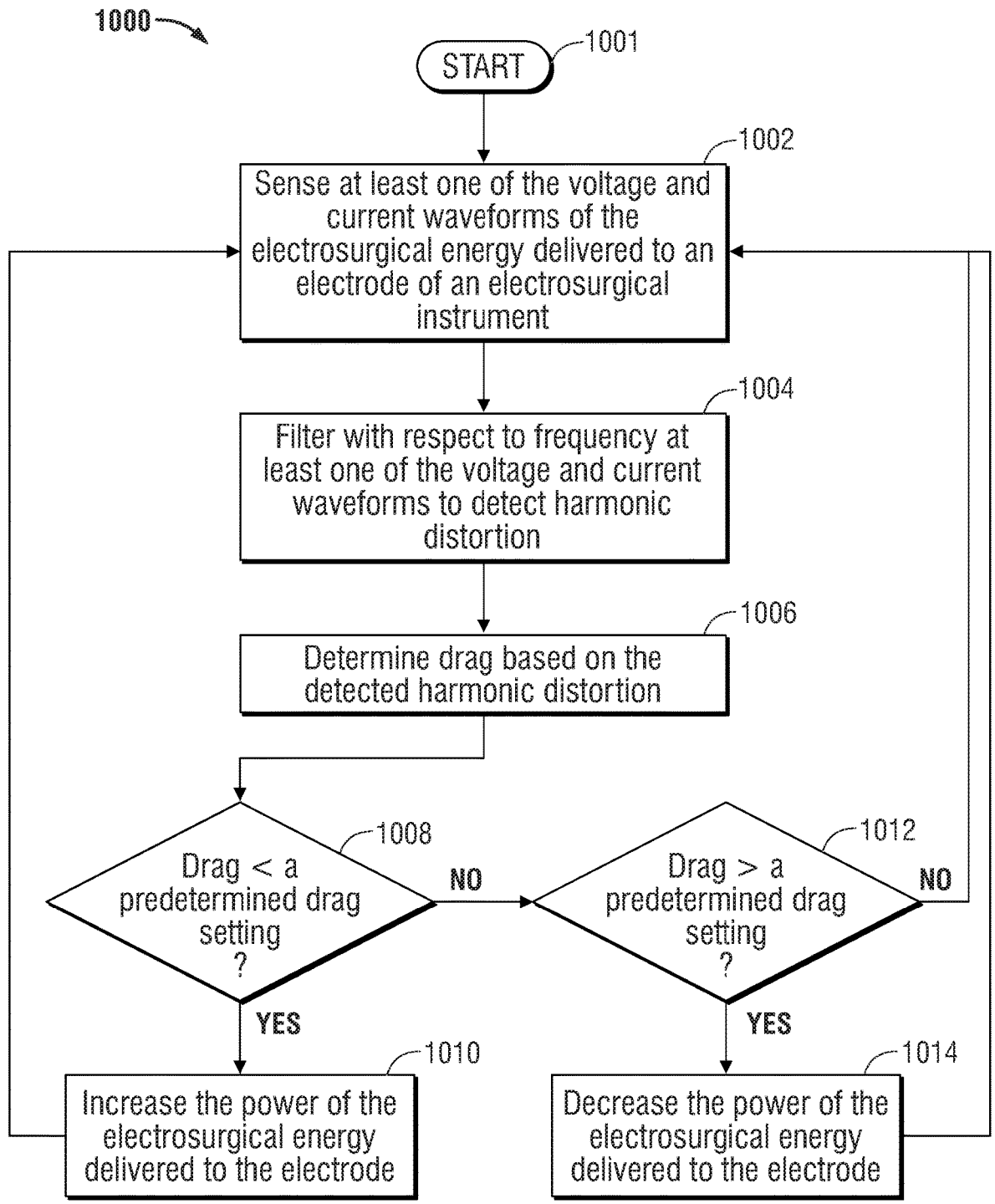
FIG. 10 is a flow diagram of a method of detecting arcing patterns based on the harmonic distortion of at least one of sensed voltage and current waveforms and controlling the cutting speed of drag on an electrosurgical instrument according to embodiments of the present disclosure.

FIG. 10 is a flow diagram of a method 1000 of controlling power delivered to an electrode of an electrosurgical instrument based on drag that is determined from an analysis of the harmonic distortion of at least one of sensed voltage and current waveforms according to embodiments of the present disclosure. After starting, in step 1001, at least one of the voltage and current waveforms of the electrosurgical energy delivered to an electrode of an electrosurgical instrument is sensed, in step 1002. In step 1004, at least one of the voltage and current waveforms are filtered with respect to frequency to detect harmonic distortion. In step 1006, drag is determined based on the determined harmonic distortion.

Next, in step 1008, it is determined whether the determined drag is less than the predetermined drag setting, e.g., provided by a surgeon via a user interface. If so, the power level of the electrosurgical energy delivered to the electrode is increased in step 1010 and the method 1000 returns to step 1002. Otherwise, in step 1012, it is determined whether the determined drag is greater than the predetermined drag setting. If it is determined that the determined drag is greater than the predetermined drag setting, the power level of the electrosurgical energy delivered to the electrode is decreased in step 1014 and the method 1000 returns to step 1002. If it is not determined that the determined drag is greater than the predetermined drag setting in step 1012, then the method 1000 returns to step 1002.

Figure 11:
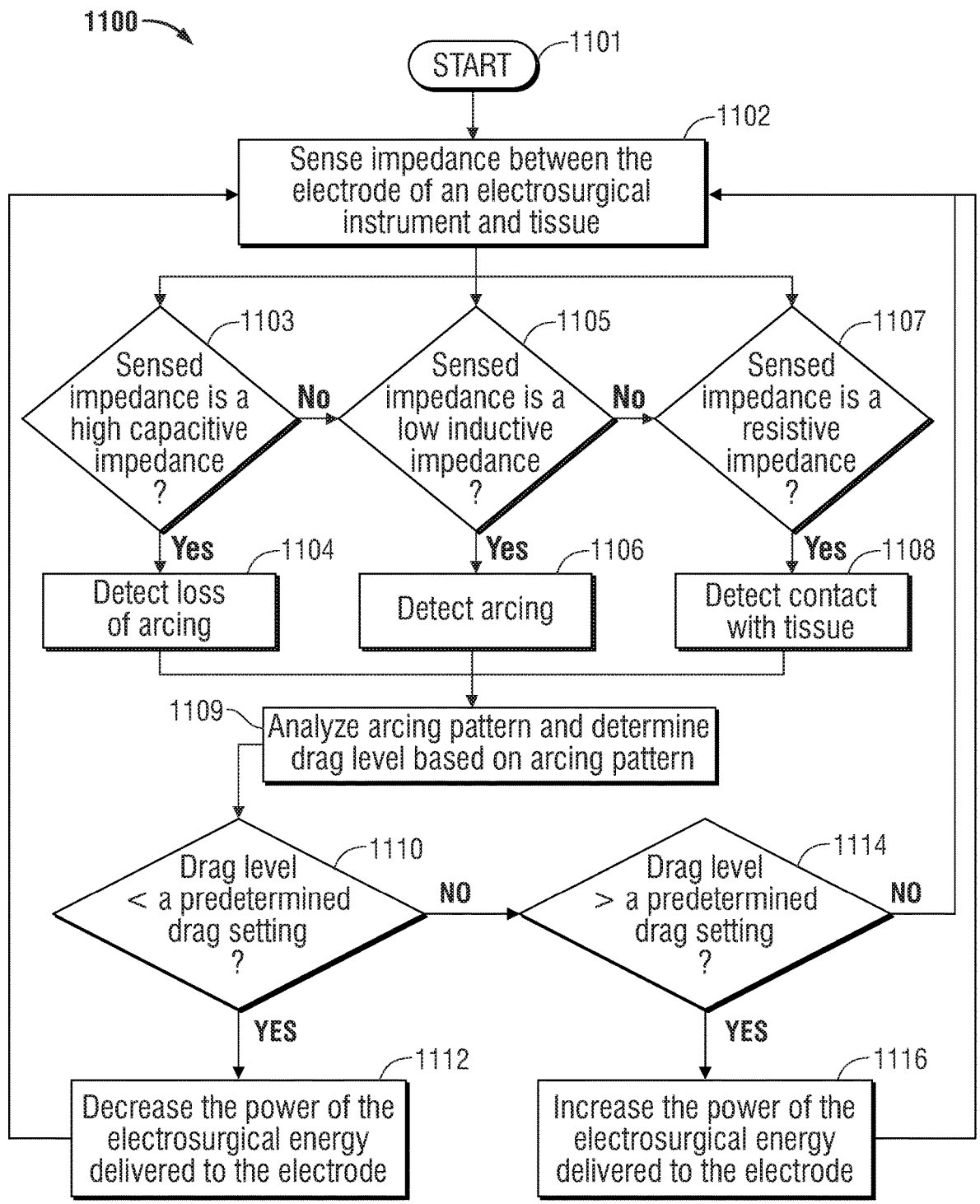
FIG. 11 is a flow diagram of a method of detecting arcing patterns based on impedance and controlling drag based on the detected arcing patterns according to embodiments of the present disclosure.

FIG. 11 is a flow diagram of a method of controlling drag based on arcing patterns determined from sensed impedance between the electrode of an electrosurgical instrument and tissue according to embodiments of the present disclosure. After starting in step 1101, impedance between the electrode and tissue is sensed in step 1102. If, in step 1103, it is determined that the sensed impedance is a high capacitive impedance, then a loss of arcing is detected in step 1104. If, in step 1105, it is determined that the sensed impedance is a low inductive impedance, then arcing is detected in step 1106. If, in step 1107, it is determined that the sensed impedance is a resistive impedance, as opposed to capacitive or inductive, then contact with tissue is detected in step 1108. Contact with tissue may first be detected when a low resistive impedance (e.g., 100-700 ohms for many types of tissues) is sensed. Then, in step 1109, the arcing pattern information obtained through steps 1102-1108 is analyzed and a drag level is determined based on the arcing pattern information.

Next, in step 1110, it is determined whether the determined drag is less than a predetermined drag setting. The predetermined drag setting may be preset in the handset, it may be automatically determined based on surgeon usage, or it may be set by the surgeon via a user interface on the handset. If it is determined that the determined drag level is less than a predetermined drag setting, the power of the electrosurgical energy delivered to the electrode is decreased in step 1112 and the method 1100 returns to step 1102. In other words, if the impedance is high, the electrode is not in contact with the tissue, thus creating a low drag condition. The power could be lowered or the voltage may be increased to increase the distance by which arcs can be established, thus increasing coagulation. In addition, the RF waveform may be changed to keep the average power constant but with a high voltage (i.e., the fulguration mode). Otherwise, in step 1114, it is determined whether the drag level is greater than the predetermined drag setting.

If it is determined that drag is greater than the predetermined drag setting, then the power of the electrosurgical energy delivered to the electrode is increased in step 1116 and the method 1100 returns to step 1102. In other words, if the impedance is a resistive impedance, then the blade is in contact with the tissue, which is a high drag condition. Thus, the power is increased to vaporize more tissue. The RF waveform may also be changed to a cut pattern to lower the voltage and increase cutting energy. If it is not determined that drag force is greater than the predetermined drag force setting, then the method 1100 returns to step 1102 to sense arcing patterns between the electrode and tissue.

If the sensed impedance stays high without arcs for an extended period, then the user has likely pulled the electrosurgical instrument 2 from the tissue. In this case, the electrosurgical generator would enter a lower-power state with just enough power for impedance sensing. Then, when the electrode makes contact with the tissue again, the controller would increase the power rapidly and then adjust for desired drag.

Figure 12:
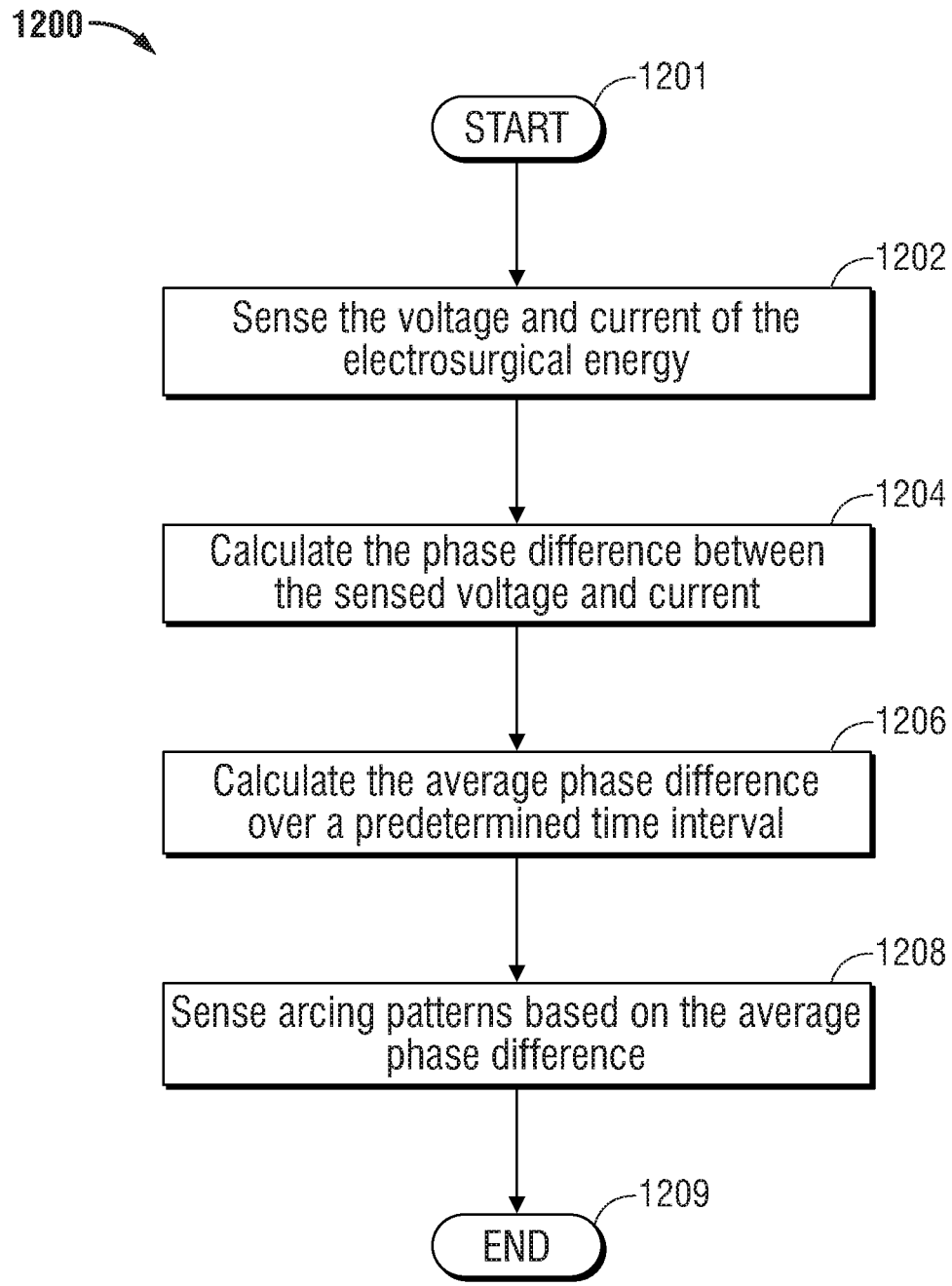
FIG. 12 is a flow diagram of a method of sensing arcing patterns based on the average phase difference according to embodiments of the present disclosure.

FIG. 12 is a flow diagram of a method 1200 of sensing arcing patterns based on the phase difference between the sensed voltage and current of the electrosurgical energy according to embodiments of the present disclosure. After starting in step 1201, the voltage and current of the electrosurgical energy is sensed 1202, e.g., by the voltage and current sensors 370, 380 of FIG. 3. In step 1204, the phase difference between the sensed voltage and current is calculated, e.g., by the controller 324, based on the sensed voltage and current. Next, in step 1206, the average phase difference over a predetermined time interval is calculated. Then, before ending at step 1209, arcing patterns are estimated in step 1208, e.g., by the controller 324, based on the calculated average phase difference over a predetermined time interval.

It is understood that any or all of the steps of the methods or processes of FIGS. 7-12 described above may be implemented in software, hardware (e.g., an FPGA), or a combination of software and hardware. In some embodiments, any or all of the steps of the methods or processes of FIGS. 7-12 described above may be implemented as program instructions stored in the memory 326 and executed by the processor 325 of the generator circuitry 300 shown in FIG. 3. In other embodiments, any or all of the steps of the methods or processes of FIGS. 7-12 that involve analyzing and/or sensing voltage and/or current waveforms may be implemented by an FPGA.

While the present invention has been particularly shown and described with reference to the preferred embodiments thereof, it will be understood by those skilled in the art that the foregoing and other changes in form and details may be made therein without departing from the spirit and scope of the invention. Therefore, the above description should not be construed as limiting, but merely as exemplifications of preferred embodiments. Those skilled in the art will envision other modifications within the scope and spirit of the present disclosure.

For example, a method of controlling electrosurgical energy would include detecting an arc and halting the RF delivery to stop the arc, as in bipolar or ligasure modes, or to encourage the arc, as in coagulation modes.

What is claimed is:

1. An electrosurgical generator for providing electrosurgical energy to an electrode of an electrosurgical instrument, the electrosurgical generator comprising:
   an output stage configured to provide electrosurgical energy to the electrode of the electrosurgical instrument;
   a sensor configured to sense at least one of a voltage waveform or a current waveform of the electrosurgical energy delivered to the electrode; and
   a controller coupled to the output stage and the sensor, the controller configured to detect harmonic distortion of the at least one of the voltage waveform or the current waveform, determine a drag force on the electrode based on the harmonic distortion, and control a level of the electrosurgical energy delivered to the electrode based on the drag force.

2. The electrosurgical generator according to claim 1, wherein the controller is configured to detect the harmonic distortion by filtering the at least one of the voltage waveform or the current waveform.

3. The electrosurgical generator according to claim 2, wherein the controller is configured to detect the harmonic distortion by applying a Fast Fourier Transform (FFT), a Discrete Fourier Transform (DFT), a Goertzel filter, or a narrow-band filter to the at least one of the voltage waveform or the current waveform.

4. The electrosurgical generator according to claim 1, wherein the controller is configured to detect the harmonic distortion by detecting at least one of a second, third, or fifth harmonic of the at least one of the voltage waveform or the current waveform.

5. The electrosurgical generator according to claim 1, wherein the sensor includes a voltage sensor and a current sensor that sense the voltage waveform and the current waveform of the electrosurgical energy.

6. An electrosurgical generator for providing electrosurgical energy to an electrode of an electrosurgical instrument, the electrosurgical generator comprising:
   an output stage configured to provide electrosurgical energy to the electrode of the electrosurgical instrument;
   a sensor configured to sense a voltage and a current of the electrosurgical energy; and
   a controller coupled to the output stage and the sensor, the controller configured to calculate an impedance based on the voltage and the current, determine a drag force based on the impedance, and control a level of the electrosurgical energy delivered to the electrode based on the drag force.

7. The electrosurgical generator according to claim 6, wherein the controller is configured to calculate a change in the impedance over time and determine the drag force based on the change in the impedance.

8. The electrosurgical generator according to claim 6, wherein the controller is configured to determine whether the impedance is a low inductive impedance, a high capacitive impedance, or a resistive impedance, and
   determine the drag force based on whether the impedance is the low inductive impedance, the high capacitive impedance, or the resistive impedance.

9. The electrosurgical generator according to claim 6, wherein the sensor includes a voltage sensor and a current sensor that sense the voltage and the current of the electrosurgical energy.

10. A method of controlling electrosurgical energy provided by an electrode of an electrosurgical instrument:
    delivering the electrosurgical energy to the electrode of the electrosurgical instrument;
    sensing at least one of a voltage waveform or a current waveform of the electrosurgical energy delivered to the electrode;
    detecting harmonic distortion of the at least one of the voltage waveform or the current waveform;
    determining drag based on the harmonic distortion; and
    controlling a level of the electrosurgical energy delivered to the electrode based on the drag.

11. The method according to claim 10, wherein detecting the harmonic distortion includes filtering the at least one of the voltage waveform or the current waveform with respect to frequency.

12. The method according to claim 10, wherein detecting the harmonic distortion includes applying a Fast Fourier Transform (FFT), a Discrete Fourier Transform (DFT), a Goertzel filter, or a narrow-band filter to the at least one of the voltage waveform or the current waveform.

13. The method according to claim 10, wherein detecting the harmonic distortion of the at least one of the voltage waveform or the current waveform includes detecting at least one of a second, third, or fifth harmonic of the at least one of the voltage waveform or the current waveform.

14. A method of controlling electrosurgical energy provided by an electrode of an electrosurgical instrument:
    delivering the electrosurgical energy to the electrode of the electrosurgical instrument;
    sensing a voltage and a current of the electrosurgical energy;
    calculating an impedance based on the voltage and the current;
    determining drag based on the impedance; and
    controlling a level of the electrosurgical energy delivered to the electrode based on the drag.

15. The method according to claim 14, further comprising:
    calculating a change in the impedance over time; and
    determining the drag based on the change in the impedance.

16. The method according to claim 14, further comprising:
    determining whether the impedance is a low inductive impedance, a high capacitive impedance, or a resistive impedance; and
    determining drag based on a result of determining whether the impedance is the low inductive impedance, the high capacitive impedance, or the resistive impedance.

* * * * *